United States Patent [19]

McRae

[11] Patent Number: Plant 5,890

[45] Date of Patent: Feb. 24, 1987

[54] ASIATIC LILLY NAMED EDITH

[75] Inventor: Edward A. McRae, Boring, Oreg.

[73] Assignee: Melridge, Inc., Gresham, Oreg.

[21] Appl. No.: 710,308

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of hybrid Asiatic lily having compact racemes of large flowers of a unique and intense cream-yellow color tone, an excellent form, and long persistence both on the plant and as cut flowers. The flowers of this new plant are particularly characterized by the unusual cream-yellow color of their large and unusually broad tepals having relatively inconspicuous maculation, these characteristics being unique in the upright Asiatic division of lilies. This plant is highly resistant to disease, shows high tolerance to virus, and is an excellent garden plant. The bulbs of this variety may be precooled and forced for cut flower production.

1 Drawing Figure

BACKGROUND OF THE INVENTION

This variety of lily plant originated as a seedling selected from a group of seedlings resulting from my crossing of an unnamed and unpatented seedling clone, having the parentage of Uncle Sam×Hallmark strain (both unpatented), with the cultivar Connecticut King (unpatented) as the pollen parent, at Sandy, Oreg. This crossing was done in the course of breeding efforts carried on by me since 1971 with the object of producing superior upright-flowering Asiatic lilies suited to cut flower production. The flowers of the new lily plant resulting from this crossing are particularly characterized by having large and very broad tepals of thick texture and a rich but soft cream-yellow coloring.

This new lily plant has also been found to possess the desirable characteristics of hybrid vigor, great hardiness, and a high degree of disease resistance. This clone also forces well for cut flower production, showing no tendency to bud abortion or leaf scorch as observed at Sandy, Oreg.

This seedling with its apparently advantageous characteristics was reproduced by me at Sandy, Oreg., by means of bulb scale propagation and natural propagation from bulblets and several generations of propagation in this manner has demonstrated that the advantageous characteristics hold true from generation to generation and appear to be firmly fixed.

DESCRIPTION OF THE DRAWINGS

My new lily plant is illustrated in the accompanying full color photographic drawing, which shows a three-quarter view of an open bloom and illustrates the flower form, tepal arrangement, and in particular the novel and distinctive rich cream-yellow color tone, as well as the unusually broad tepals with their inconspicuous maculation.

DESCRIPTION OF THE NEW PLANT

The following is a detailed description of my new hybrid Asiatic lily with the color designations according to The R.H.S. Colour Chart published by The Royal Horticultural Society of London, England.

THE PLANT

Origin: Seedling.

Parentage:

*Seed parent.*—An unnamed and unpatented seedling clone having the parentage of Uncle Sam×Hallmark strain (both unpatented).

*Pollen parent.*—Connecticut King (unpatented).

Classification:

*Botanic.*—Hybrid lily cultivar, Division 1-A, R.H.S. Horticultural Classification of Lilies.

*Commercial.*—Upright Asiatic hybrid lily.

Form: Single stem, erect, and tall.

Height: 100 to 130 cm. above ground level from bulbs 12 to 15 cm. in circumference.

Growth: Vigorous and sturdy.

Foliage:

*Quantity.*—Abundant.

*Leaf size.*—6 to 8 cm. long and 1 to 1.5 cm. wide.

*Leaf shape.*—Lanceolate with entire margins.

*Texture.*—Leathery.

*Aspect.*—Glabrous and glossy.

*Color.*—Light to medium green.

Bulbs:

*Size.*—Ranging up to 25 cm. in circumference.

THE BUD

Form: Long ovoid and obtuse.

Size:

*Length.*—7 to 9 cm. just prior to opening.

Opening rate: The bud opens slowly at maturity, in response to light.

Color: Cream-Yellow, RHS 3 B/C, when outer tepals first divide and when tepals begin to unfurl.

Peduncle:

*Length.*—7 to 10 cm., depending upon light levels.

*Color.*—Medium green with soft purple overlay when temperature is not too hot.

THE FLOWER

Blooming habit: Annually. Once, and profusely, in mid-season for Asiatic lilies. October dug bulbs, properly precooled and planted in February in western Oregon under glass, with no supplementary lighting, will flower in an average of 80 to 85 days.

Size: Large. 14 to 18 cm. in diameter.

Borne: In a compact raceme, 6 to 8 flowers on a single stem.

Shape: Flat to slightly cup-shaped; tepal tips lightly recurved.

Tepalage:

*Number.*—Six.

*Arrangement.*—Imbricated.

*Color.*—Rich Cream-Yellow, RHS 3 B/C. There are a few tiny pigmented papillae in the extreme center of the inner tepals, parallel to the nectary furrows, and of deep magenta color.

Color change: The color deepens slightly as the flowers age, becoming closer to RHS 3B, not to RHS 3C.

Pedicels:

*Length.*—5 to 12 cm. with no secondary buds.

*Form.*—Sturdy.

*Color.*—Light green with soft plum overlay when in cool temperatures.

Fragrance: None.

Persistence: The flower is long lasting both on the plant and as a cut flower.

Disease resistance: The flower and plant are resistant to disease; in particular, they are resistant to Fusarium and Botrytis as observed in Oregon.

REPRODUCTIVE ORGANS

Stamens:

*Number.*—Six, in arrangement typical of genus Lilium.

Anthers:

*Color.*—Greyed Gold, RHS 167A.

*Filaments.*—Length: 5 cm. Color: Ivory or soft cream-yellow.

Pollen:

*Color.*—Greyed Gold, RHS 167A.

Pistils:

*Number.*—One.

*Style.*—Length: About 5 cm.

*Stigma.*—Color: Light green to soft cream-yellow, overlaid with medium purple.

Characteristics of ovary: Typical of genus Lilium.

THE FRUIT

Fertility: The fruit is fertile.

Shape: Ovoid.

Color at Maturity: Soft brown, sometimes overlaid with light plum.

My new variety of hybrid Asiatic lily most nearly resembles the unpatented variety Connecticut King but it has clear cream-yellow flowers rather than the deep yellow of Connecticut King. The flowers of the new plant have much broader tepals than those of Connecticut King and its inflorescence is better in form in that it does not carry straggly secondary buds. The new variety forces more rapidly and is less susceptible to bud abortion and scorch.

I claim:

1. A new and distinctive variety of hybrid Asiatic lily, substantially as herein shown and described, characterized by its high resistance to disease and tolerance to virus; its vigorous growth; its excellent flower form and substance; and its versatility both as a garden plant and as a plant produced from precooled bulbs forced for cut-flower production; and in particular, its unique rich cream-yellow coloring and inconspicuous maculation.

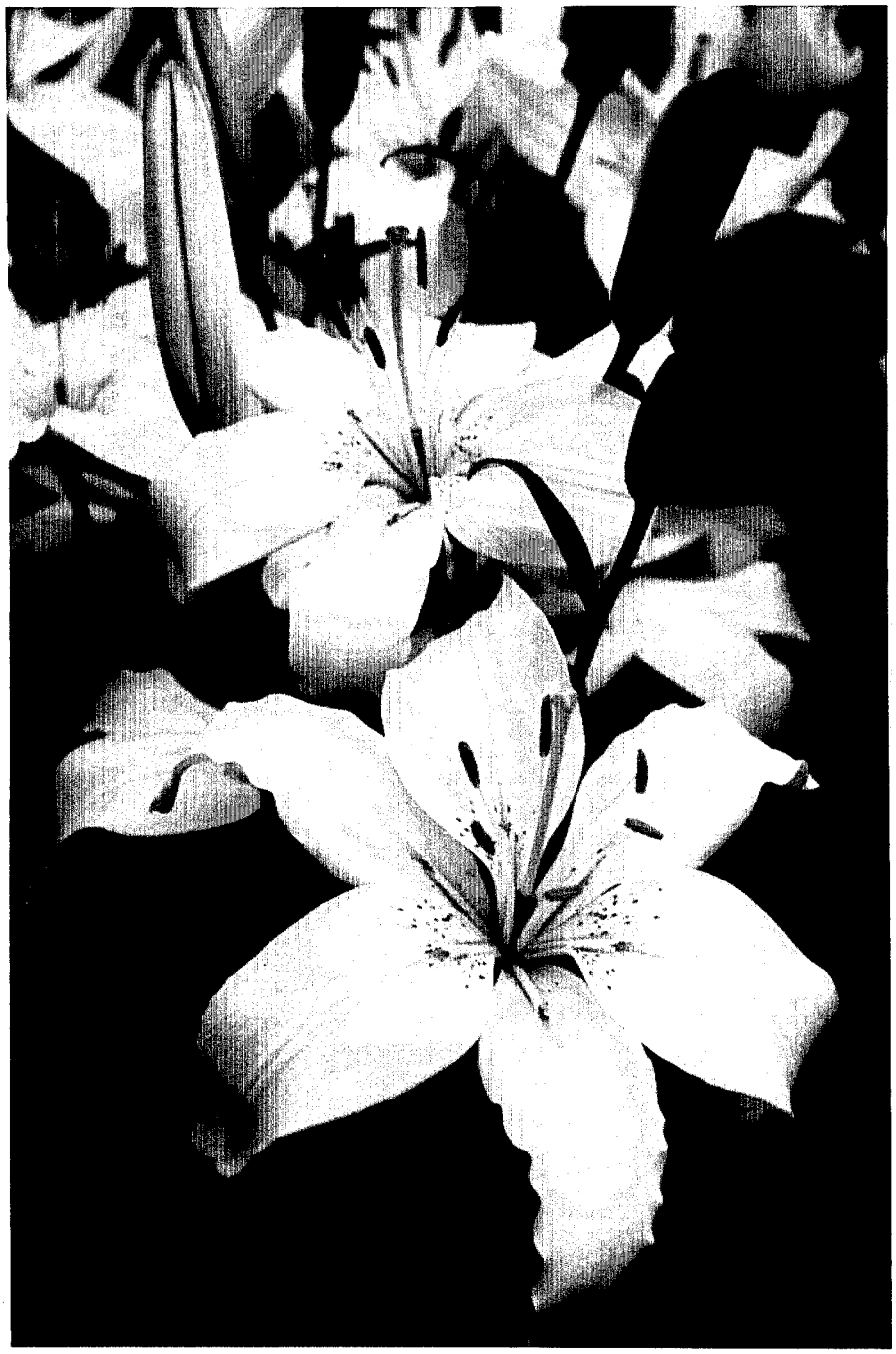

* * * * *